Figure 1:
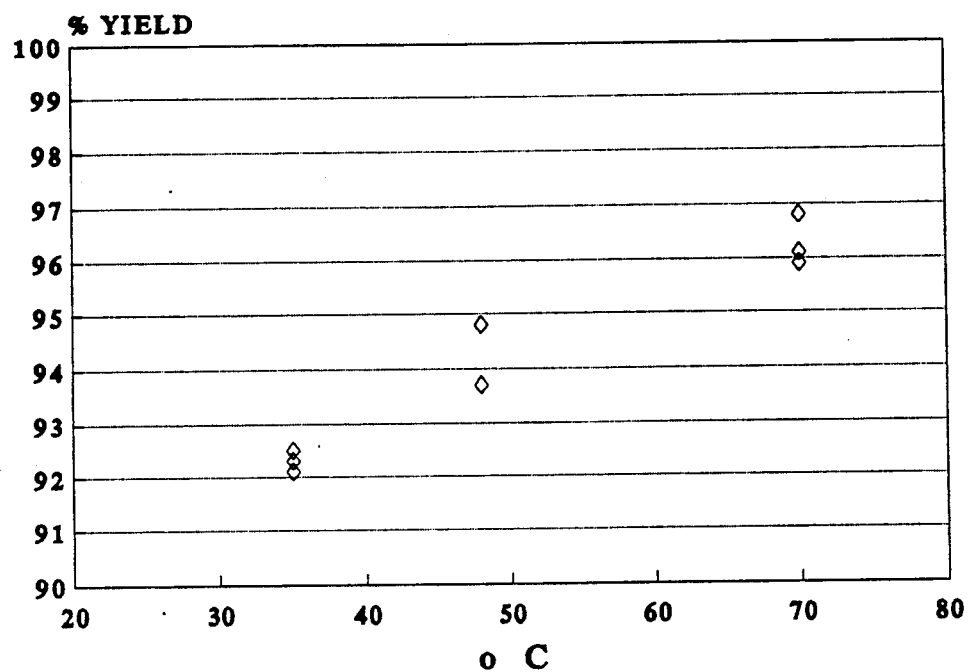

United States Patent [19]

Schwindeman et al.

[11] Patent Number: 5,332,533
[45] Date of Patent: Jul. 26, 1994

[54] ALKYLLITHIUM PROCESS

[75] Inventors: James A. Schwindeman, Charlotte; Robert C. Morrison, Gastonia; B. Troy Dover, Kings Mountain; John F. Engel, Belmont; Conrad W. Kamienski, Gastonia; Randy W. Hall; Douglas E. Sutton, both of Kings Mountain, all of

[73] Assignee: FMC Corporation, Philadelphia, Pa.

[21] Appl. No.: 87,582

[22] Filed: Jul. 6, 1993

[51] Int. Cl.$^5$ .............................................. C07F 1/02
[52] U.S. Cl. .............................................. 260/665 R
[58] Field of Search .................................. 260/665 R

[56] References Cited

U.S. PATENT DOCUMENTS 3,122,592  2/1964  Eberly ............................ 260/665 R
3,452,112  7/1969  Kamienski ..................... 260/665

OTHER PUBLICATIONS

Conrad W. Kamienski, The Journal of Organic Chemistry, vol. 34, (1969) No. 4, pp. 1116–1121.
Henry Gilman et al., Journal of American Chemical Society, vol. 63, pp. 2479–2482 (1941).
Henry Gilman et al., Journal of American Chemical Society, vol. 62 pp. 2327–2335 (1940).
Cong-yuan Guo, Journal of American Chemical Society, 1985, 107, pp. 6028–6030.
Robert N. Mealsi, The Journal of Organic Chemistry, vol. 9, pp. 211–218 (1944).

*Primary Examiner*—José G. Dees
*Assistant Examiner*—Porfirio Nazario-Gonzalez
*Attorney, Agent, or Firm*—Charles C. Fellows; Robert L. Andersen

[57] ABSTRACT

A high temperature process for producing alkyllithium compounds in high yields of at least 90% and high purity comprising reacting, in a liquid hydrocarbon solvent, an alkyl halide containing 3 to 16 carbon atoms and mixtures thereof with lithium metal particles of less than 300 microns in size at a temperature between 35° and 125° C. and recovering the alkyllithium compound.

14 Claims, 7 Drawing Sheets

ALKYLLITHIUM PROCESS

The present invention concerns a high temperature process for preparing alkyllithium compounds containing 2 to 16 carbon atoms by reacting lithium metal with alkyl halides at temperatures of 35° to 120° C.

Methods of preparation of alkyllithiums have been published by various workers in the field, such as, for example, C. W. Kamienski et al. U.S. Pat. No. 3,452,112. A process for producing alkyllithium containing six or more carbon atoms, such as octyllithium is disclosed by C. Guo and coworkers, J. Am. Chem. Soc., 1985, 107, 6030 who employed a refluxing hexane medium and a four hour post addition reflux to obtain a yield of about 70%.

High purity concentrated alkyllithiums are highly desired as it is important that the alkyllithium product be free from or at least low in olefin content as olefins lead to the development of deep yellow colored alkyllithium products. The level of chloride ion impurities is important as high chloride values of 300 ppm and above generally occur in hazy alkyllithium products. While concentrated, clear solutions of alkyllithiums in hydrocarbon solvents are clearly desirable, they are difficult to obtain. One reason for this is that concentrated solutions of alkyllithium compounds are highly viscous so that unreacted excess lithium generally employed in the reaction is very difficult to remove by filtration or other conventional particle separation means. The prior art processes produce alkyllithium compounds containing over 300 parts per million of dissolved inorganic halides, generally lithium chloride, which is not removed by filtration. When these dilute solutions are concentrated by distillation or other solvent solvent removal means, the lithium halide forms fine crystals in the product solution which gives the product a hazy rather than clear appearance and in some instances, the halide precipitates. High yields of alkyllithium, 90% or greater, is highly desirable economically.

The present invention provides an improved process for producing alkyllithium in high yields and high purity by reacting a primary alkyl halide with lithium metal in a liquid hydrocarbon solvent in an inert atmosphere to obtain yields of alkyllithiums of at least 90% by reacting an alkyl halide containing 2 to 16 carbon atoms and mixtures thereof with finely divided lithium metal in a hydrocarbon solvent at a temperature between 35 and 125 degrees centigrade.

The preferred reaction temperatures vary from compound to compound, with each compound having its own preferred conditions. Surprisingly, within a preferred temperature range for an alkyl halide/lithium metal reaction, the most preferred reaction condition occurs at reflux conditions. For example, the reaction that produces butyllithium conducted at 35° C. and 50° C. under reflux conditions results in higher yields and higher purity than are achieved when conducting the same reaction at 35° C. or 50° C. under non-reflux conditions. This can be seen in the Table by comparing Run 7742 with Run 7743 and Run 7746 with Run 7747. Comparison of Run 7742 with 7743 illustrates that in the lower temperature range, reacting at reflux (35° C.), improves the yield and slightly decreases the soluble chloride level. Comparison of Runs 7746 and 7747 illustrate that near the middle of the temperature range, 50° C., reacting at reflux increases the yield and significantly decreases the soluble chloride level. The increase in yield of butyllithium with increasing temperature can also be seen in FIG. 1, a plot of yield versus temperature for the lithium metal butylchloride reaction to produce butyllithium, showing a preferred range of 35° to 60° C. and most preferably at 50° C.

Figure 3:
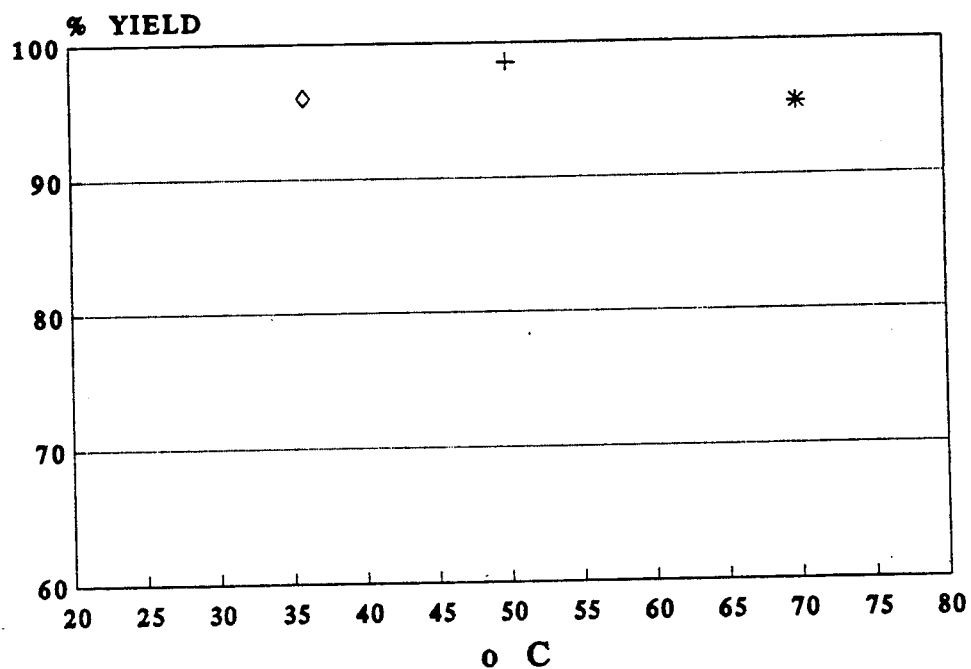

The use of high reaction temperatures in alkylchloride/lithium reactions not only improves yields of the alkyllithium but also improves reaction initiation and promotes completion of the respective alkyl chloride reactions, thus decreasing the by-product coupling and disproportionation reactions. These phenomena are evident, not only by the increased yields obtained, but also by the lower amounts of dissolved inorganic chloride and olefins present in the product solutions. The Table 1 data generally support the conclusion that for a selected alkyl chloride the yield improves as the reaction temperature is increased. However, there is for each alkyl chloride an optimum temperature which, if exceeded, causes the yield to decrease. n-Butyl chloride reacted with lithium in refluxing solvents is shown in FIG. 3 to increase to a high yield of 98.5% at about 50° C. and to decrease slightly at 70° C. to 95.3%. When this butylchloride-lithium metal reaction is done in toluene at 80° C. the yield drops to 86.6 (Run 7824).

The lithium metal used in this process can be any clean lithium metal and preferably containing 0.4 to 0.76% sodium. Excess lithium metal in amounts of up to 10% by weight above stoichiometric amounts are used to insure reaction of all the alkyl chloride used in a reaction. To best achieve the benefits of this process the lithium metal is used in particulate form, preferably less than 300 microns in size, most preferably 10 to 300 microns in size. Typically commercially available lithium dispersions containing 0.5 to 0.76% sodium are used but pure lithium metal dispersions can also be successfully employed.

The alkyl halides used in this process are typically made from alcohols so the alkyl halides may contain some residual alcohol which may be catalytic. All examples in this application were conducted with commercially available alkyl halides. The useful alkyl halides contain 2 to 16 carbon atoms and the halide ion may be bromo, chloro or iodo with chloro being preferred as being less expensive and more generally available.

Solvents suitable for use in the process of this invention include liquid saturated aliphatic and cycloaliphatic hydrocarbons containing 5 to 12 carbon atoms such as isopentane, n-pentane, n-hexane, n-heptane, 2-ethylhexane, iso-octane, n-octane, decane, dodecane and the like or saturated cyclic hydrocarbons containing 5 to 12 carbon atoms such as cyclopentane or methylcyclohexane and the like and mixtures thereof. Aromatic hydrocarbons containing 6 to 12 carbon atoms such as benzene, toluene, n-propyl benzene, isopropylbenzene, xylenes 1,2,3,4,tetrahydronaphthalene and the like may also be used. Since reflux conditions and optimum reaction temperatures are related, hydrocarbon mixtures are quite useful. Nevertheless, a single liquid hydrocarbon may be more desirable than mixed hydrocarbons.

As noted above reaction temperatures of 35° to 125° C. can be employed and while each alkyl halide has its own preferred reaction temperature curve and specific best reaction temperature the best results are obtained under reflux conditions. Long reaction times can be used at lower temperatures but give poorer results than are achieved under reflux conditions. The alkyl halide feed rate can be varied. Slow alkyl halide feed rates with external heat may be used; heat may be applied to help initiate the reaction and the feed rate adjusted to control the exothermic reaction. Reaction initiation is faster if the lithium metal/hydrocarbon mixture is at the reflux temperature of the solvent when the alkyl halide feed is started but no major increases in yields occur from this procedure. The reaction media should be cooled or allowed to cool to ambient conditions once the reaction is completed. The post reaction heating taught by Meals, J. Org. Chem., 9, pp 211-218 (1944) should be avoided.

Numerous experiments were conducted under inert conditions employing various commercially available alkyl chlorides and commercially available lithium metal dispersions having particles sizes of less than 300 microns. The lithium dispersion was washed in solvent to remove the dispersing oil and rinsed until the metal was clean, free of oil. The clean metal was added to the selected solvent in a reactor equipped with a reflux condenser, a stirrer, a feed device for adding the alkyl chloride and means for heating the reactor and reaction mass. Surprisingly, the metal conditioner taught by Kamienski et al. in U.S. Pat. No. 3,452,112 is not needed in the present process. The lithium-solvent mixture was stirred and heated to the selected reaction temperature, often the reflux temperature of the solvent, and the alkyl chloride feed was started. Thereafter, the temperature was controlled by the rate of alkyl chloride addition. Process variables such as reaction temperatures, halide feed rate, excess lithium, percent sodium in the lithium, washing the lithium and the effect these variables have on yield and purity were extensively studied. The reactions are conducted in an inert atmosphere. The results are contained in the various figures and the Table which summarizes a wide variety of compounds and conditions. In general the table shows yields and optimable temperature for each alkyl halide. Optimable temperatures for each alkyl chloride produces minimal soluble chloride levels. The chloride analytical technique used had a lower detection limit of <13 ppm.

FIG. 1—This plot shows the % yield of n-butyl lithium (◊) prepared in hexane using 10% excess lithium containing 0.48% sodium at several temperatures increases in yield with increasing temperature.

Figure 2:
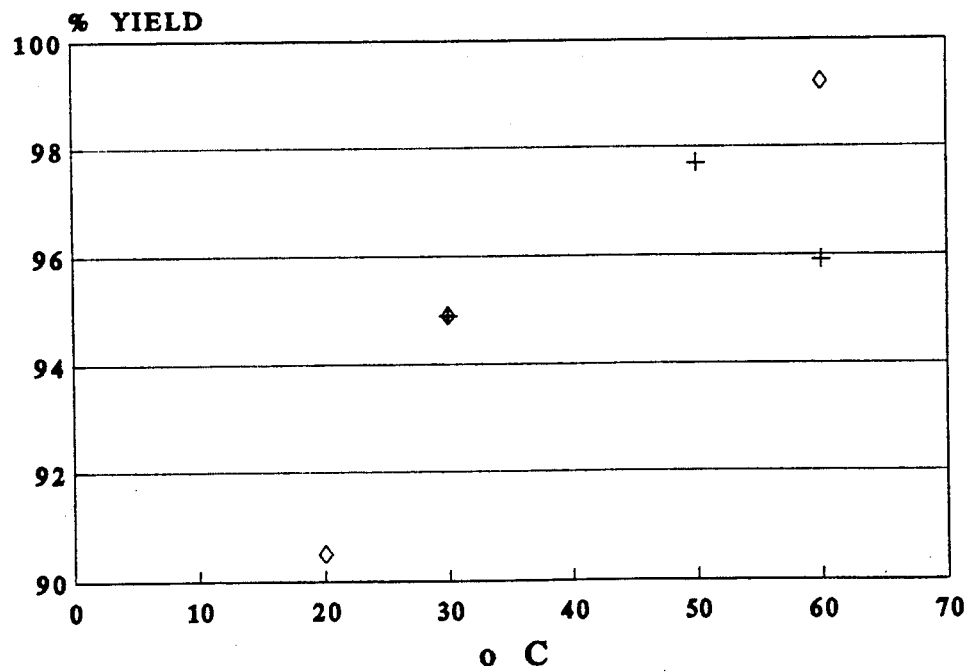

FIG. 2—This plot shows the results of a comparable series of experiments in which the solvent used was toluene. Again, increasing temperature definitely increased yield. The lithium contained 0.76% sodium. "Dry" toluene, 30 ppm $H_2O$ (◊) and "wet" toluene, 226 ppm $H_2O$ (+).

FIG. 3 shows a series of n-butyl lithium experiments using 10% excess lithium (0.48% Na) in refluxing solvents: pentane boiling point (BP) 36.1° C. (◊), cyclopentane BP 49.3° C. (+) and hexane BP 68.7° C. (*). FIG. 3 clearly shows the yield increasing with temperature but then starting to decrease with further increasing temperature.

Figure 4:
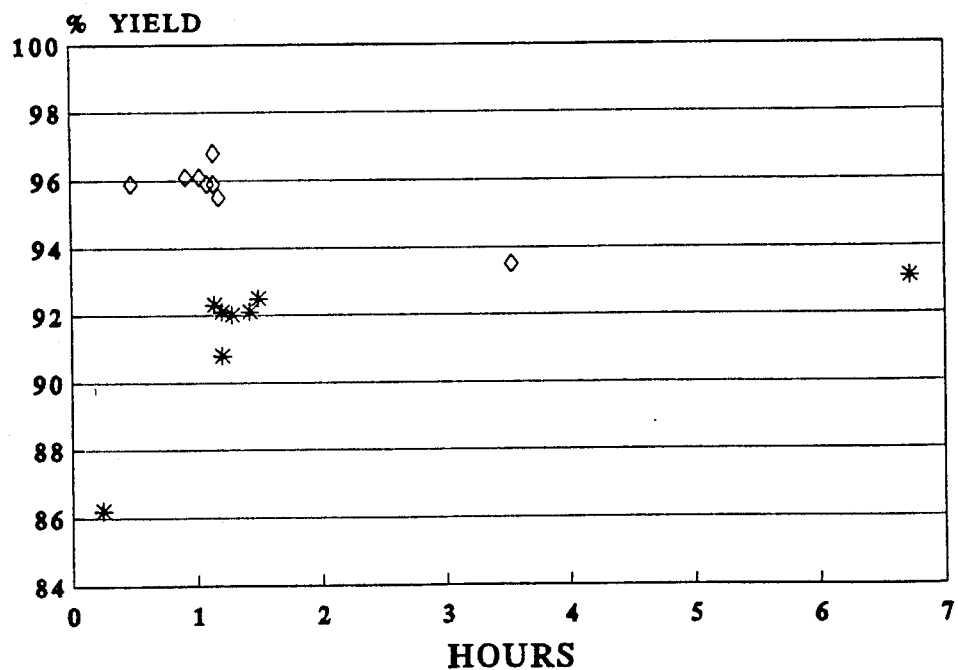

FIG. 4 shows the results of varying the feed rate of n-butyl chloride dispersion in hexane. At 35° C. (*) the yield gradually increased although very slightly. At reflux (◊) there is no change in yield at short feed times, 0.5 to 1.5 hours, but the yield drops at longer feed times.

Figure 5:
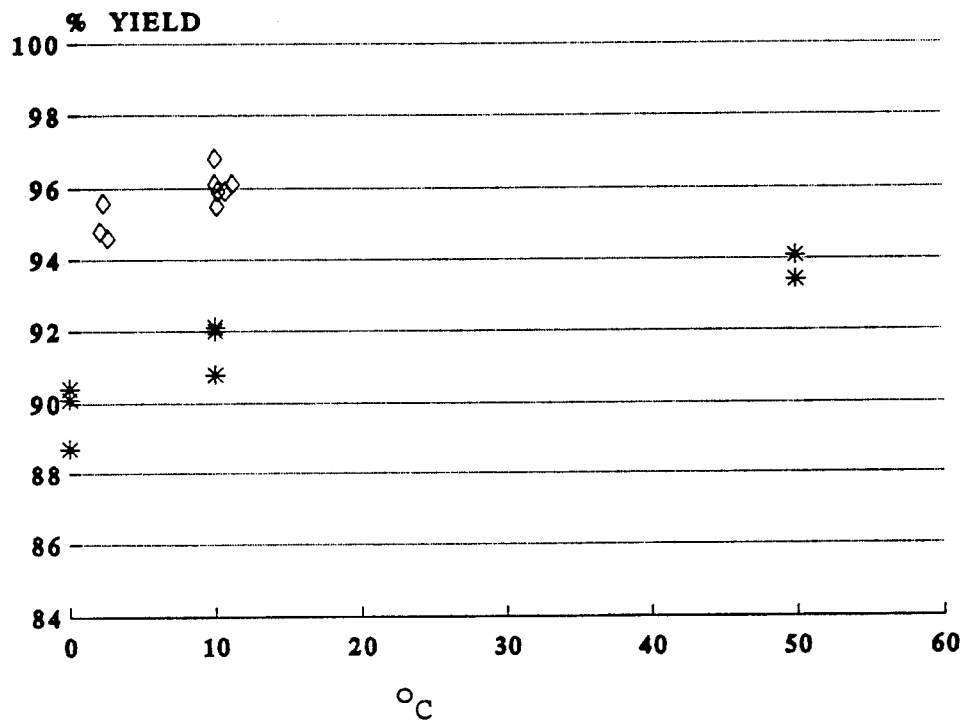

FIG. 5—This plot shows results of varying the amount of lithium metal in producing n-butyllithium. Yield drop off is only slightly less sensitive to reaction temperature at reflux (◊) compared to reaction at 35° C. (*), about a 1% decrease at reflux versus a 2% drop off at 35° C. Greater than 10 mole % excess lithium results in same yield improvement.

Figure 6:
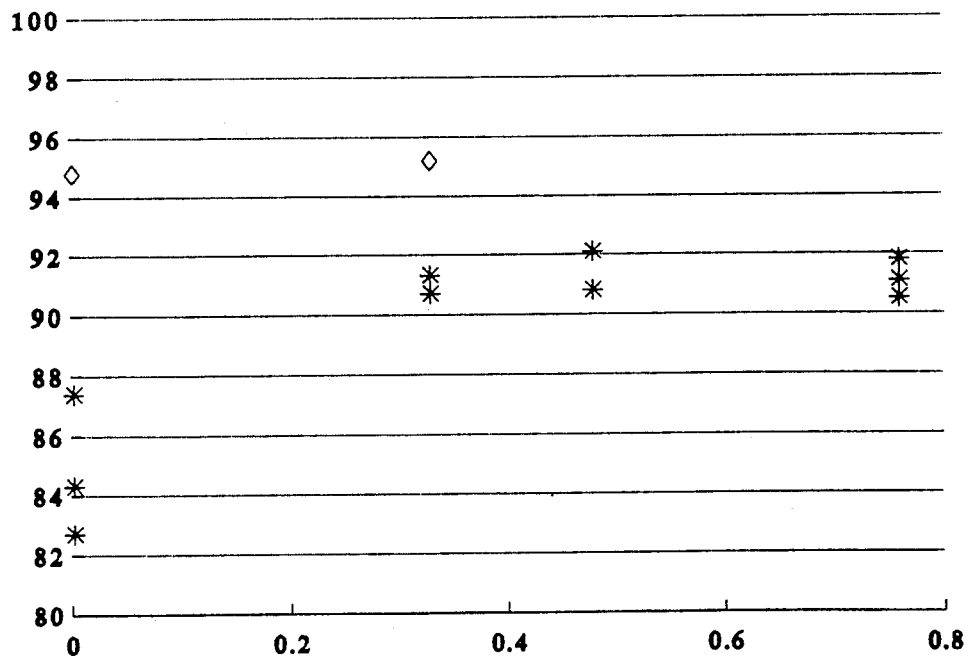

FIG. 6—This plot shows that n-butyllithium yields decrease significantly at alloyed levels of sodium in the lithium metals below 0.3 to 0.4% when the butyl chloride/lithium reaction is conducted at 35° C. (*) but there is no decrease at reflux ( ).

Figure 7:
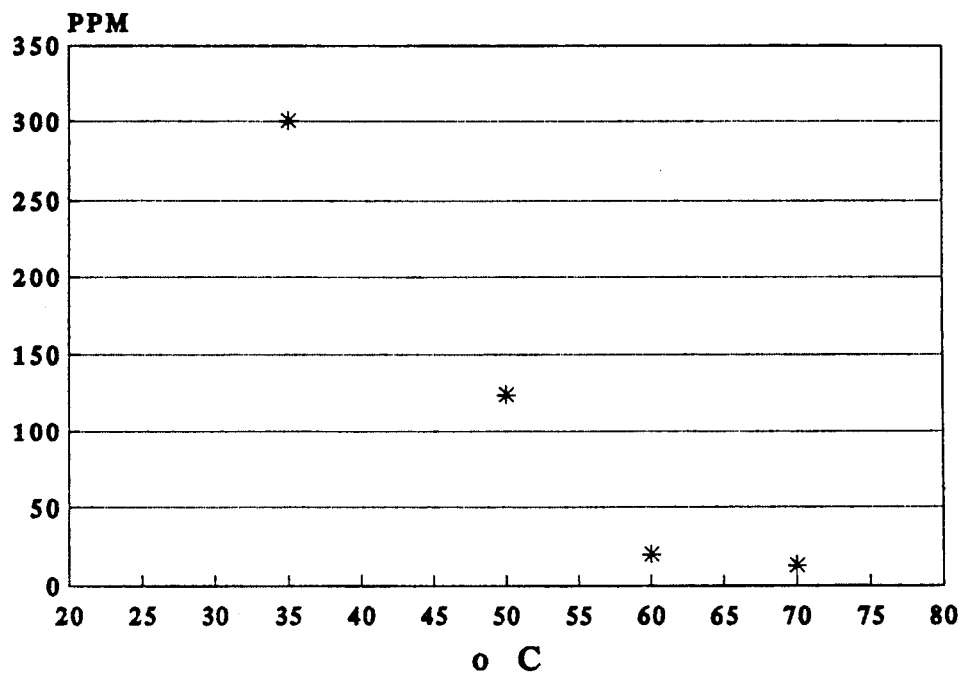

FIG. 7—This plot shows that, as the reaction temperatures are increased in hexane, soluble inorganic chloride levels in the n-butyllithium product decrease significantly (*).

Figure 8:
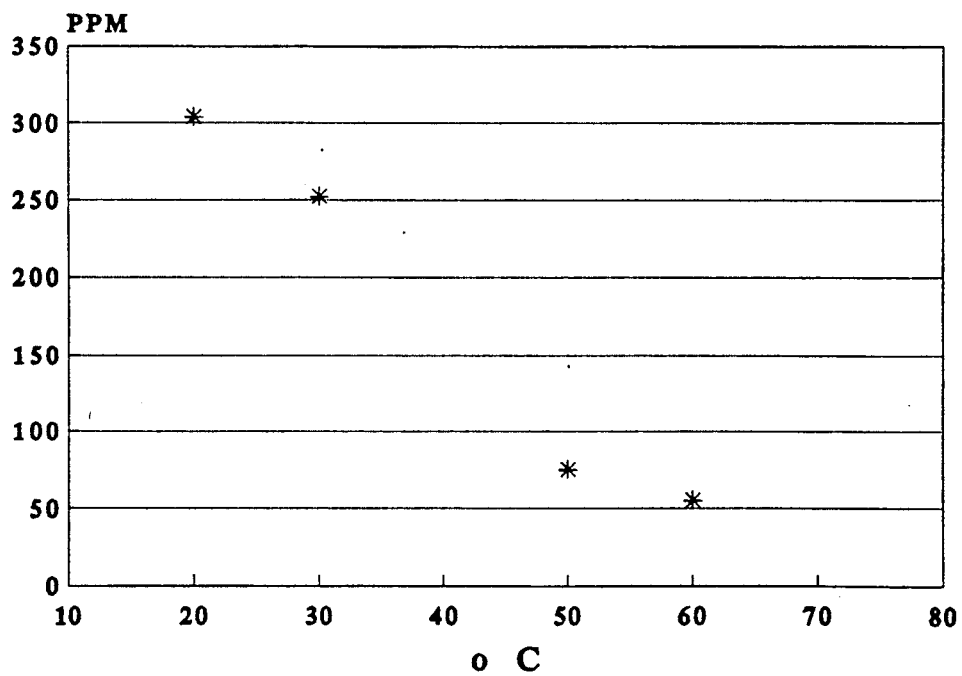

FIG. 8—This plot shows that, as the reaction temperatures (*) are increased in toluene, soluble inorganic chloride levels in the n-butyllithium product decrease significantly.

Figure 9:
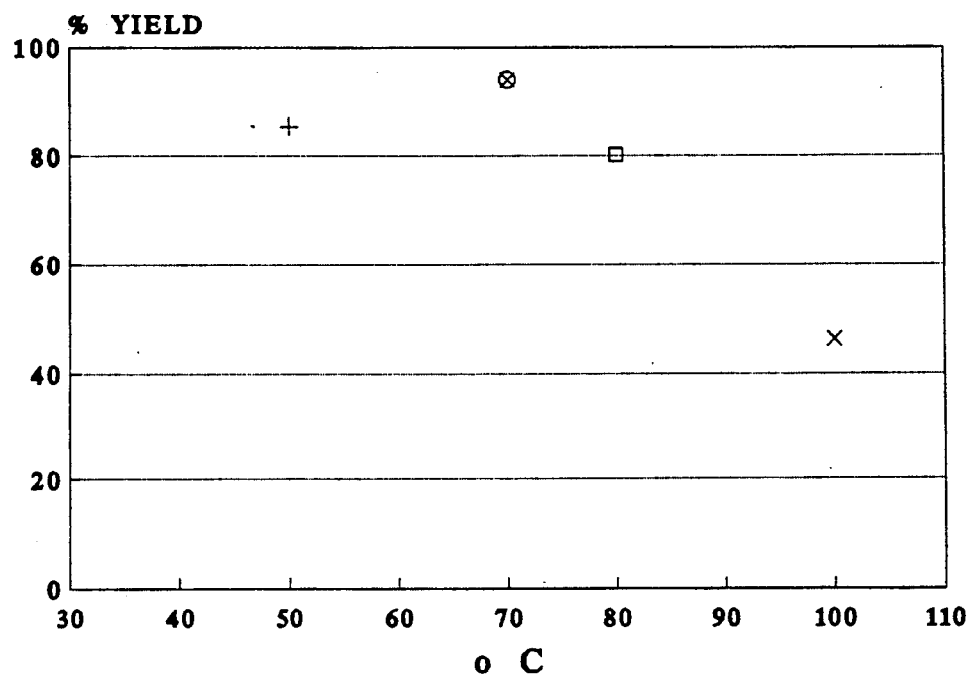

FIG. 9—This plot shows an optimum hexyllithium yield in refluxing solvents at about 70° C. Cyclopentane (+), hexane (o), cyclohexane (□) and heptane (x).

Figure 10:
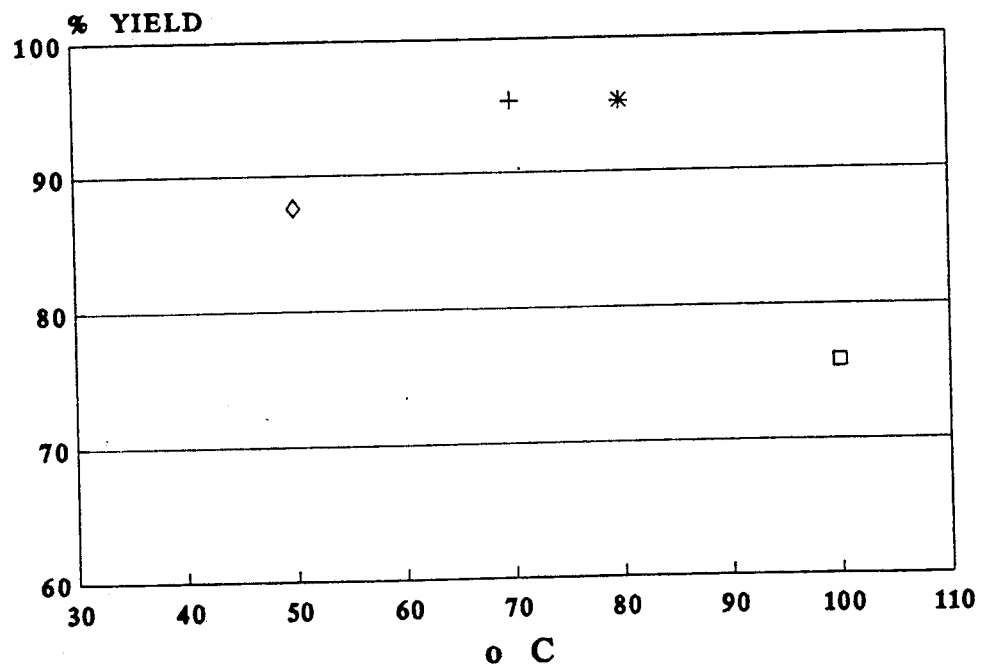

FIG. 10—This plot shows octyllithium yields in refluxing solvents are highest between 70° and 80° C. Solvents employed: cyclopentane ( ), hexane (+), cyclohexane (*) and heptane (□).

Figure 11:
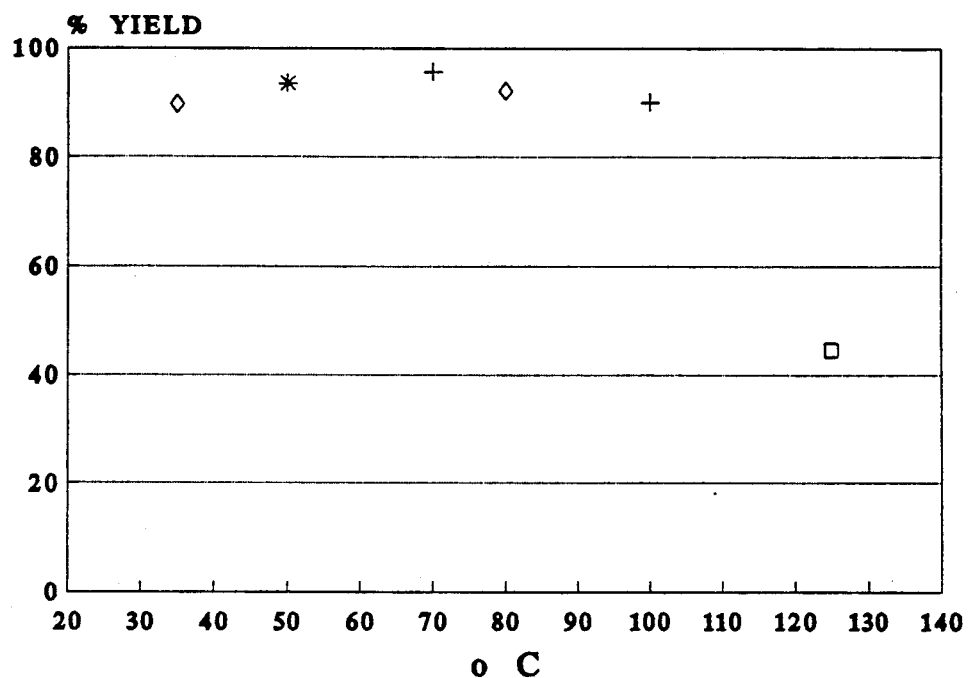

FIG. 11—This plot shows the yields of 2-ethylhexyllithium in various refluxing solvents. Solvents employed were cyclohexane (o), heptane (+), cyclopentane (*) and octane (o).

Figure 12:
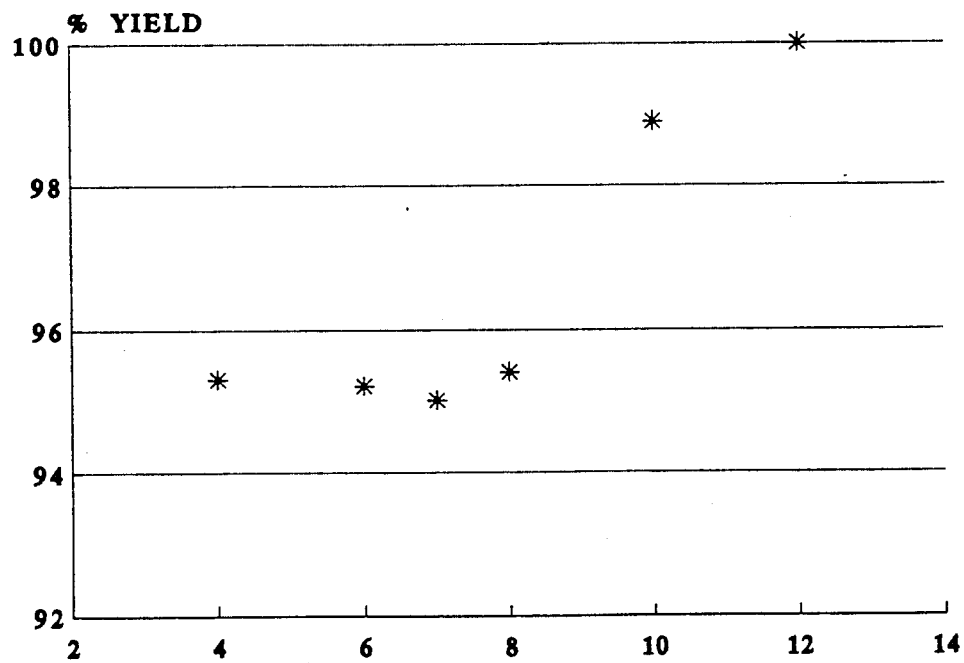

FIG. 12—This plot further emphasizes the excellent yields of various alkyllithiums obtained in refluxing hexane. The alkyllithiums tested were butyl, hexyl, octyl, decyl and dodecyllithium.

Figure 13:
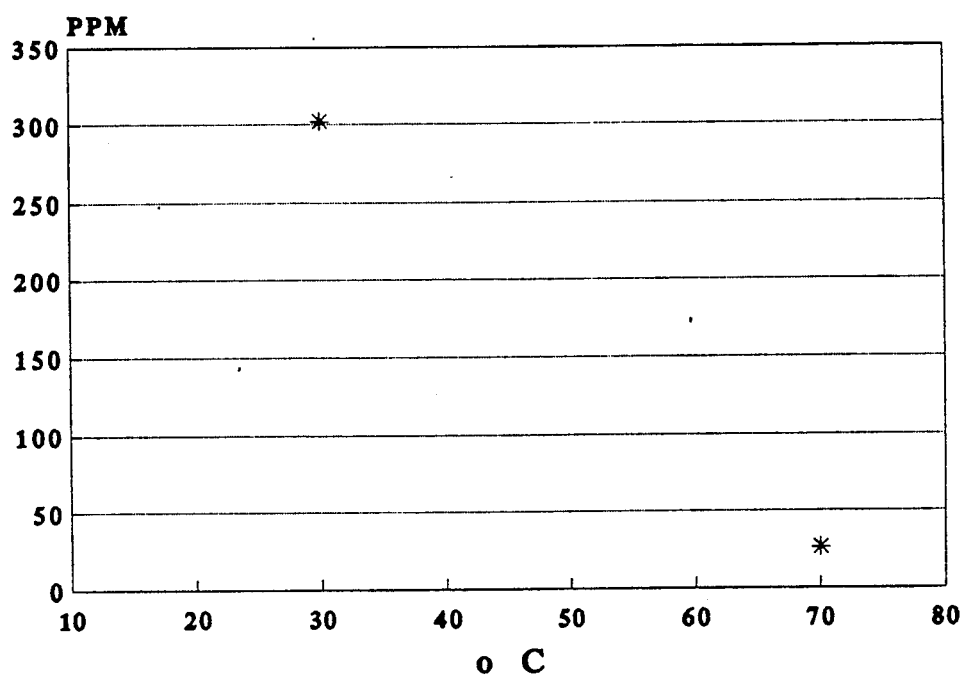

FIG. 13 shows that n-hexyllithium soluble inorganic chloride values are lower when the reaction is done at a higher temperature.

The following examples further illustrate the invention. Unless noted otherwise all examples were conducted in an inert argon atmosphere.

EXAMPLE 1

PREPARATION OF n-BUTYLLITHIUM AT ELEVATED TEMPERATURE Run 7739

The reactor and apparatus consisted of a 500 ml Morton Cleaved 3 necked flask equipped with a reflux condensor, Y tube for additions, 125 ml pressure-equalizing addition (dropping) funnel, stirring shaft with teflon blade, stirring motor, a thermometer probe with an electronic read out and means for maintaining an inert atmosphere in the reactor.

A commercially available lithium metal dispersion having a particle size of less than 300 microns was hexane washed twice and pentane washed once and dried with argon. The metal was then weighed, 12.10 g (1.743 moles).

Hexane, 310 milliliters, was used to transfer the lithium through a transfer tube to the reactor. The hexane-lithium mixture was heated to reflux (Dry Ice/hexane in condensor) and dropwise feed of n-butyl chloride begun. The reaction proceeded instantaneously (heavy refluxing) and the source of heat was removed. The 73.4 g of n-butylchloride (0.7924 moles) was fed in over a 40 minute period, the reaction heat controlled strictly by the rate of reflux. The reaction mixture was allowed to cool to ambient, with stirring, over a 2.5 hour period. The mixture was filtered and the lithium chloride residue washed three times with hexane (50 ml each) over a 25-30 minute period. The combined filtrate and washings were weighed. A sample of the product solution was assayed for total contained alkalinity and color index was determined and the yield of n-butyllithium was calculated.

EXAMPLE 2

ELEVATED TEMPERATURE, REFLUX EXAMPLE Run 7622, 414-43 1-HEXYLLITHIUM HEXANE

A 500 ml, three-necked Morton flask was fitted with a mechanical stirrer, a 250 ml, pressure-equalizing addition funnel, and a Claisen adapter equipped with a reflux condenser, a thermocouple, and an argon inlet. This apparatus was dried in an oven overnight at 125° C., assembled hot, and allowed to cool to room temperature in a stream of argon. Lithium dispersion, 22.00 g (3.17 mole, 20% excess Li, 2.40 equivalents) was washed free of mineral oil with hexane ($2 \times 100$ ml), pentane ($1 \times 100$ ml), dried in a stream of argon, then transferred to the flask with 210 ml of hexane. The resultant slurry was stirred at 470 RPMs and heated to 66° C. After reflux was established, the heat source was removed. 1-Hexyl chloride, 159.32 g (1.32 mole, 1.00 equivalent), was added dropwise through the addition funnel. The reaction temperature rose rapidly to reflux. The reaction mixture was maintained at reflux by adjustment of the halide feed rate. The total halide feed time was 3.25 hours. At the end of the feed, the reaction temperature rapidly declined. The reaction mixture was stirred for one hour at 470 RPMs, two hours at 300 RPMs, then transferred to a scintered glass filter. The solution filtered very rapidly, 300 ml of filtrate was collected in 1.5 minutes at 2 psi argon. The solids were reslurried with fresh hexane ($2 \times 50$ ml), and these washes were combined with the main filtrate.

This afforded a clear, dark yellow solution, yield=450 ml, 329.5 g. Total base=34.9% Active C-Li=34.7% The yield based on the active C-Li (carbon-lithium) analysis was 94.1% Soluble Cl (chloride) <26 ppm

EXAMPLE 3

ELEVATED TEMPERATURE, NON-REFLUX EXAMPLE Run 7853, 442-3 2-ETHYLHEXYLLITHIUM IN HEPTANE

A one liter, three-necked Morton flask was fitted with a mechanical stirrer, a 250 ml, pressure-equalizing addition funnel, and a Claisen adapter equipped with a reflux condenser, a thermocouple, and an argon inlet. This apparatus was dried in an oven overnight at 125° C., assembled hot, and allowed to cool to room temperature in a stream of argon. Lithium dispersion, 18.50 g (2.67 mole, 20% excess Li, 2.40 equivalents) was washed free of mineral oil with pentane three times ($3 \times 100$ ml), dried in a stream of argon, then transferred to the flask with 400 ml of heptane. The resultant slurry was stirred at 470 RPMs, then heated to 70° C. with a heating mantle. The mantle was then removed, and 2-ethylhexyl chloride, 165.03 g (1.11 mole, 1.00 equivalent), was added dropwise through the addition funnel. The reaction temperature slowly rose, after approximately 3% of the feed had been added. The temperature was maintained between 70° C. and 75° C. with intermittent cooling from an hexane/dry ice cooling bath. The total halide feed time was 2.25 hours. At the end of the feed, the reaction temperature rapidly declined. The reaction mixture was stirred for one hour at 470 RPMs, one hour at 300 RPMs, then transferred to a scintered glass filter. The solution filtered very rapidly, 600 ml of filtrate was collected in one minute at 2 psi argon. The solids were reslurried with fresh heptane (65 ml, 60 ml), and these washes were combined with the main filtrate.

This afforded a clear, colorless solution, yield=700 ml, 480.4 g. Total base=27.3% Active C-Li=27.3% The yield based on the active C-Li analysis was 98.4% Soluble Cl <13 ppm.

EXAMPLE 4

ELEVATED TEMPERATURE, REFLUX EXAMPLE Run 8507, 442-60 1-OCTYLLITHIUM IN HEXANE

A one liter, three-necked Morton flask was fitted with a mechanical stirrer, a 250 ml pressure-equalizing addition funnel, and a Claisen adapter equipped with a thermocouple, a reflux condenser, and an argon inlet. This apparatus was dried in an oven overnight at 125° C., assembled hot, and allowed to cool to room temperature in a stream of argon. Lithium dispersion, 20.50 g (2.953 mole, 20% excess Li, 2.40 equivalents) was washed free of mineral oil with hexane ($2 \times 100$ ml) pentane ($1 \times 100$ ml), dried in a stream of argon, then transferred to the reaction flask with 450 ml of hexane. The resultant slurry was stirred at 450 RPMs, and heated to 67° C. with a heating mantle controlled with a variac. After reflux was established, the heat source was removed. 1-Chlorooctane, 182.97 g (1.231 mole, 1.00 equivalent) was added dropwise through the addition funnel. An immediate exotherm was observed. The reaction temperature rose rapidly to reflux. The reaction mixture was maintained at reflux by adjustment of the halide feed rate. The total halide feed time was 100 minutes. The reaction temperature declined rapidly at the end of the halide feed. The reaction mixture was stirred for one hour at 450 RPMs, 1.25 hours at 300 RPMs, then transferred to a dry, scintered glass filter with argon pressure. The solution filtered very rapidly, as 550 ml of filtrate was collected in 2.167 minutes at 3 psi argon. The solids were reslurried with fresh hexane ($2 \times 75$ ml), and these washes were combined with the main filtrate.

This afforded a clear, pale yellow solution, yield=790 ml, 548.7 g. Total base=25.6%. Active C-Li=24.6% The yield based on the active C-Li (carbon-lithium) analysis was 91.4%. Soluble Cl (chloride)=31 ppm.

A one ml aliquot of this solution was hydrolyzed with water at low temperature. The organic layer was analyzed by Gas Chromatography. The components were identified by co-elution with authentic standards. The composition of the hydrolyzed sample was analyzed as: n/octane (93.84%), 1-chlorooctane (1.77%), and side reaction products, (coupling, disproportionation) (4.38%).

COMPARISON EXAMPLE A

Run 7605 414-32 1-HEXYLLITHIUM IN HEXANE

A 500 ml, three-necked Morton flask was fitted with a mechanical stirrer, a 250 ml, pressure-equalizing addition funnel, and a Claisen adapter equipped with a reflux condenser, a thermocouple, and an argon inlet. This apparatus was dried in an oven overnight at 125° C., assembled hot, and allowed to cool to room temperature in a stream of argon. Lithium dispersion, 9.00 g (1.30 mole, 20% excess, 2.40 equivalents), pentane ($1 \times 100$ ml), dried in a stream of argon, then transferred to the flask with 170 ml of hexane. The resultant slurry was stirred at 470 RPMs. 1-Hexyl chloride, 65.13 g (0.54 mole, 1.00 equivalent), was added dropwise through the addition funnel. The reaction temperature slowly rose, after approximately 3% of the feed had been added. The temperature was maintained between 30° C. and 35° C. with intermittent cooling from an hexane/dry ice cooling bath. The total halide feed time was 2 hours. At the end of the feed, the reaction temperature rapidly declined. The reaction mixture was stirred for thirty minutes at 470 RPMs, 1.5 hours at 300 RPMs, then transferred to a scintered glass filter. The solids were reslurried with fresh hexane (2×35 ml), and these washes were combined with the main filtrate.

This afforded a clear, pale yellow solution, yield=240 ml, 168.4 g. Total base=24.6% Active C-Li=24.6% The yield based on the active C-Li analysis was 81.7%. Soluble Cl=302 ppm.

COMPARISON EXAMPLE B

Run 8518, 442-63 1-OCTYLLITHIUM IN HEXANE

A one liter, three-necked Morton flask was fitted with a mechanical stirrer, a 250 ml pressure-equalizing addition funnel, and a Claisen adapter equipped with a thermocouple, a reflux condenser, and an argon inlet. This apparatus was dried in an oven overnight at 125° C., assembled hot, and allowed to cool to room temperature in a stream of argon. Lithium dispersion, 21.50 g (3.098 mole, 20% excess Li, 2.40 equivalents) was washed free of mineral oil with hexane (3×100 ml), pentane (1×100 ml), dried in a stream of argon, then transferred to the reaction flask with 480 ml of hexane. The resultant slurry was stirred at 450 RPMs, and heated to 35° C. with a heat gun. The heat source was removed. 1-Chlorooctane, 191.95 g (1.291 mole, 1.00 equivalent) was added dropwise through the addition funnel. An exotherm was noted after 2% of the feed had been added. The reaction mixture was maintained at 30°-35° C. by a dry ice/hexane cooling bath. The total halide feed time was 108 minutes. The reaction temperature declined rapidly at the end of the halide feed. The reaction mixture was stirred for one hour at 450 RPMs, 1.25 hours at 300 RPMs, then transferred to a dry, scintered glass filter with argon pressure. The solution filtered very slowly, as 550 ml of filtrate was collected in 15 minutes at 3 psi argon. The solids were reslurried with fresh hexane (2×75 ml), and these washes were combined with the main filtrate.

This afforded a clear, pale yellow solution, yield=800 ml, 563.8 g. Total base=23.9%. Active C-Li=23.3% The yield based on the active C-Li (carbon-lithium) analysis was 84.8%. Soluble Cl (chloride)=208 ppm.

A one ml aliquot of this solution was hydrolyzed with water at low temperature. The organic layer was analyzed by Gas Chromatography. The components were identified by co-elution with authentic standards. The composition of the hydrolyzed sample was n-octane (81.14%), 1-chlorooctane (4.31%), and side reaction products (coupling, disproportionation)(11.55%).

TABLE

| RXN | HALIDE | SOLVENT | RXN TEMP (O C.) | YIELD | SOL. CL (ppm) | COMMENTS |
|---|---|---|---|---|---|---|
| 7728 | n-Butylchloride | Hexane | 35 | 91.9 | 240 | |
| 7730 | n-Butylchloride | Hexane | 35 | 91.6 | 289 | |
| 7743 | n-Butylchloride | Hexane | 35 | 90.1 | 398 | |
| 7746 | n-Butylchloride | Hexane | 50 | 93.7 | 299 | |
| 7752 | n-Butylchloride | Hexane | 50 | 93.7 | 124 | |
| 7755 | n-Butylchloride | Hexane | 50 | 94.8 | | |
| 7812 | n-Butylchloride | Hexane | 70 | 95.2 | 30 | Reflux |
| 7813 | n-Butylchloride | Hexane | 70 | 94.7 | 30 | Reflux |
| 7840 | n-Butylchloride | Hexane | 70 | 95.5 | <13 | Reflux |
| 7843 | n-Butylchloride | Hexane | 70 | 95.9 | <13 | Reflux |
| 7945 | n-Butylchloride | Hexane | 70 | 96.1 | <13 | Reflux |
| 7849 | n-Butylchloride | Hexane | 70 | 95.5 | 13 | Reflux |
| 7742 | n-Butylchloride | Pentane | 35 | 95.9 | 378 | Reflux |
| 7747 | n-Butylchloride | Cyclopentane | 50 | 98.5 | 135 | Reflux |
| 7756 | n-Butylchloride | Toluene | 20 | 90.5 | 304 | |
| 7712 | n-Butylchloride | Toluene | 35 | 95.2 | 252 | |
| 7733 | n-Butylchloride | Toluene | 35 | 94.6 | | |
| 7753 | n-Butylchloride | Toluene | 50 | 97.4 | 64 | |
| 7788 | n-Butylchloride | Toluene | 50 | 97.9 | 86 | |
| 7748 | n-Butylchloride | Toluene | 60 | 99.2 | 16 | |
| 7749 | n-Butylchloride | Toluene | 60 | 95.9 | 94 | |
| 7824 | n-Butylchloride | Toluene | 80 | 86.6 | 20 | |
| 7864 | 1-Chloro-2-methylbutane | Hexane | 70 | 98.4 | <13 | Reflux |
| 7605 | 1-Chlorohexane | Hexane | 35 | 81.7 | 302 | |
| 7622 | 1-Chlorohexane | Hexane | 70 | 94.1 | <26 | Reflux |
| 7650 | 1-Chlorohexane | Hexane | 70 | 94.0 | 27 | Reflux |
| 7905 | 1-Chlorohexane | Hexane | 70 | 93.7 | 62 | Reflux |
| 7713 | 1-Chlorohexane | Cyclopentane | 50 | 85.4 | 205 | Reflux |
| 7696 | 1-Chlorohexane | Cyclohexane | 80 | 80.2 | <26 | Reflux |
| 7691 | 1-Chlorohexane | Heptane | 100 | 46.1 | 15210 | Reflux |
| 7701 | 1-Chlorohexane | Heptane | 70 | 93.9 | 48 | |
| 7871 | 1-Chlorohexane | Toluene | 60 | 98.1 | 15 | |
| 7863 | 1-Chloroheptane | Hexane | 70 | 95.0 | <13 | Reflux |
| 7734 | 1-Chlorooctane | Cyclopentane | 50 | 87.6 | 250 | Reflux |
| 8516 | 1-Chlorooctane | Hexane | 35 | 83.0 | 158 | |
| 8518 | 1-Chlorooctane | Hexane | 35 | 84.8 | 208 | |
| 7629 | 1-Chlorooctane | Hexane | 70 | 95.4 | 90 | Reflux |
| 8507 | 1-Chlorooctane | Hexane | 70 | 91.4 | 31 | Reflux |
| 8512 | 1-Chlorooctane | Hexane | 70 | 91.8 | 38 | Reflux |
| 7685 | 1-Chlorooctane | Cyclohexane | 80 | 95.3 | <21 | Reflux |
| 7681 | 1-Chlorooctane | Heptane | 100 | 75.8 | 379 | Reflux |
| 7714 | 1-Chloro-2-ethylhexane | Cyclopentane | 50 | 93.3 | 25 | Reflux |
| 7853 | 1-Chloro-2-ethylhexane | Heptane | 70 | 98.4 | <13 | |

TABLE-continued

| RXN | HALIDE | SOLVENT | RXN TEMP (O C.) | YIELD | SOL. CL (ppm) | COMMENTS |
|---|---|---|---|---|---|---|
| 7678 | 1-Chloro-2-ethylhexane | Heptane | 70 | 95.6 | 96 | |
| 7680 | 1-Chloro-2-ethylhexane | Heptane | 100 | 89.8 | 39 | Reflux |
| 7700 | 1-Chloro-2-ethylhexane | Cyclohexane | 80 | 91.9 | <10 | Reflux |
| 7741 | 1-Chloro-2-ethylhexane | Octane | 125 | 44.4 | | Reflux |
| 7754 | 1-Chlorodecane | Hexane | 70 | 98.9 | 27 | Reflux |
| 7787 | 1-Chlorododecane | Hexane | 70 | 100.0 | 20 | Reflux |
| 8044 | 1-Chlorododecane | Cyclopentane | 50 | 78.4 | 461 | Reflux |
| 8046 | 1-Chlorododecane | Cyclopentane | 50 | 82.3 | 146 | Reflux, held for add. 3.5 hr reflux |
| 8037 | 1-Chlorododecane | Toluene | 60 | 81.8 | 71 | |
| 8041 | 1-Chlorododecane | Toluene | 80 | 88.5 | 27 | |
| 8048 | 1-Chlorododecane | Toluene | 110 | 59.4 | 34 | Reflux |

What is claimed is:

1. In the process for producing alkyllithium compounds by reacting in a liquid hydrocarbon solvent selected from liquid saturated aliphatic hydrocarbons containing 5 to 12 carbon atoms, saturated liquid cycloaliphatic hydrocarbons containing 5 to 12 carbon atoms and liquid aromatic hydrocarbons containing 6 to 12 carbon atoms and mixtures thereof, an alkyl halide containing 3 to 16 carbon atoms with lithium metal particles of less than 300 microns in size in which the improvement consists of producing the alkyllithium compounds in high yields of at least 90% and high purity, containing less than 300 ppm dissolved lithium halide, by conducting the reaction under conditions selected from: conducting the reaction under reflux conditions in hydrocarbon solvents which reflux at temperatures between 50° C. and 100° C.; and conducting the reaction under non-reflux conditions at temperatures between 50° C. and 125° C. and recovering the alkyllithium compound.

2. The process of claim 1 wherein the alkyl halide is an alkyl chloride containing 3 to 16 carbon atoms.

3. The process of claim 1 wherein the alkyl halide is butyl chloride and the reaction temperature is between 35° and 70° C.

4. The process of claim 1 wherein the alkyl halide is 1-chloro-2-methylbutane and the reaction temperature is between 50° and 80° C.

5. The process of claim 1 wherein the alkyl halide is 1-chlorohexane and the reaction temperature is between 50° and 80° C.

6. The process of claim 1 wherein the alkyl halide is 1-chlorohexane and the reaction temperature is between 60° and 80° C.

7. The process of claim 1 wherein the alkyl halide is 1-chloroheptane and the reaction temperature is between 60° and 80° C.

8. The process of claim 1 wherein the alkyl halide is 1-chlorooctane and the reaction temperature is between 55° and 85° C.

9. The process of claim 1 wherein the alkyl halide is 1-chloro-2-ethylhexane and the reaction temperature is between 50° and 90° C.

10. The process of claim 1 wherein the alkyl halide is 1-chlorodecane and the reaction temperature is between 50° and 90° C.

11. The process of claim 1 wherein the alkyl halide is 1-chlorododecane and the reaction temperature is between 50° and 85° C.

12. An alkyllithium composition consisting of alkyllithium compound of high purity, containing 3 to 16 carbon atoms, in a liquid hydrocarbon solvent selected from liquid saturated aliphatic hydrocarbons containing 5 to 12 carbon atoms, saturated liquid cycloaliphatic hydrocarbons containing 5 to 12 carbon atoms and liquid aromatic hydrocarbons containing 6 to 12 carbon atoms containing 3 to 16 carbon atoms and mixtures thereof, and containing less than 300 ppm dissolved lithium halide.

13. An alkyllithium composition of claim 12 containing less than 200 ppm dissolved lithium halide.

14. An alkyllithium composition of claim 12 in wherein the alkyllithium is n-butyllithium and the composition contains less than 100 ppm dissolved lithium halide.

* * * * *